Figure 1:
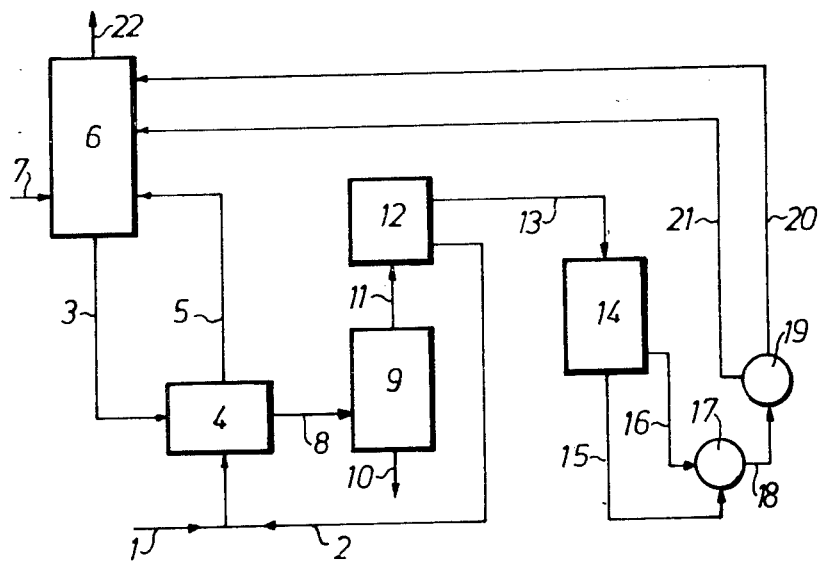

United States Patent [19]

Fischer et al.

[11] 3,954,567
[45] May 4, 1976

[54] EVAPORATING SOLUTIONS WHICH CONTAIN PHOSGENE IN A VACUUM LIQUID RING PUMP

[75] Inventors: Peter Fischer, Odenthal-Osenau; Wilhelm Hagen, Leverkusen; Helmut Klappert; Walter Levin, both of Cologne; Karl-Friedrich Zenner; Johannes Werneburg, both of Dormagen, all of Germany

[73] Assignee: Bayer Aktiengesellschaft, Leverkusen, Germany

[22] Filed: Aug. 28, 1973

[21] Appl. No.: 392,360

[30] Foreign Application Priority Data
Aug. 30, 1972 Germany............................ 2242626

[52] U.S. Cl.................................. 203/86; 203/87; 260/453 A; 417/68
[51] Int. Cl.² ............................................ B01D 3/00
[58] Field of Search .... 260/544 K, 453 PH, 453 SP; 203/42, 91, 87, DIG. 14, 74, 75, 77, 2

[56] References Cited
UNITED STATES PATENTS

| | | | |
|---|---|---|---|
| 1,972,157 | 9/1934 | Miller | 203/91 |
| 2,489,703 | 11/1949 | Cook et al. | 203/91 |
| 3,102,083 | 8/1963 | Adams | 203/91 |
| 3,175,969 | 3/1965 | Slover | 203/75 |
| 3,228,860 | 1/1966 | Larson | 203/2 |
| 3,505,176 | 4/1970 | Buchsbaum et al. | 203/DIG. 14 |
| 3,549,504 | 12/1970 | Adica et al. | 203/91 |

Primary Examiner—Norman Yudkoff
Assistant Examiner—Frank Sever
Attorney, Agent, or Firm—Lawrence S. Pope; Gene Harsh

[57] ABSTRACT

Solutions of phosgene, an organic solvent and nitrogen or oxygen compounds which have a higher boiling point than the solvent are evaporated in a vacuum which is produced by a liquid ring pump operated on a phosgene-containing solvent as working fluid, the used working fluid being subsequently returned to the process.

5 Claims, 6 Drawing Figures

EVAPORATING SOLUTIONS WHICH CONTAIN PHOSGENE IN A VACUUM LIQUID RING PUMP

This invention relates to a process for the evaporation in a vacuum of solutions which contain phosgene, an organic solvent and nitrogen or oxygen compounds which have a higher boiling point than the solvent.

Numerous continuously operated commercial processes are known for reacting organic nitrogen or oxygen compounds with excess phosgene with the elimination of hydrogen chloride, for example the preparation of isocyanates from primary amines, the preparation of N,N-disubstituted carbamic acid chlorides from secondary amines or the preparation of chloroformic acid esters of carbonic acid esters from alcohols or phenols.

These reactions are usually carried out in the inert organic solvent which has a lower boiling point than the end product, partly in order to suppress the formation of unwanted by-products such as ureas of carbodiimides by diluting the starting compounds and partly in order to keep the intermediate products or end products which are solid at room temperature, such as aminohydrochlorides, carbamic acid chlorides or isocyanates, in a liquid form as solutions or suspensions.

In the phosgenation apparatus, the hydrogen chloride formed in the reaction separates from the liquid phase and carries part of the excess, unreacted phosgene with it in the vapour form. Most of the phosgene taken up by the hydrogen chloride can be recovered by absorption in an absorber through which cooled solvent is trickled. Gaseous or liquid phosgene may be introduced into the absorber at the same time in order to adjust the phosgene solution to the required concentration for the reaction with the nitrogen compound or oxygen compound introduced.

The solution or suspension discharged from the phosgeneration apparatus, which consists of phosgene, organic solvent and nitrogen compounds which have a higher boiling point than the solvent, must be evaporated to recover the solvent. This evaporation is preferably carried out in a vacuum in order to preserve the temperature sensitive end products.

The apparatus at present used in the art for producing the vacuum in continuously operated plants are steam jet suction pumps, oil lubricated rotary vane pumps, rotary piston pumps or piston pumps.

Phosgene which remains undissolved or is not completely dissolved in the distillate obtained by the distillation of the solvent enters the vacuum source and is discharged from there either into the waste gas or, if it is decomposed by moisture, into the effluent water. Apart from the fact that the absorption of phosgene by water results in the formation of hydrochloric acid by a decomposition reaction so that all parts of the plant which come into contact with the acid must be made of acid resistant material, solvent in the vapour form is also liable to contaminate the vacuum source and pass from there into the effluent water or the waste gas.

It is an object of this invention to provide a process in which no incompletely dissolved phosgene enters the vacuum source and from there the waste gas or effluent water. Apart from protecting the vacuum source against attack by the flow medium, the invention is mainly directed towards protecting the environment against pollution. According to the invention, this problem is reducced or substantially obviated producing the vacuum by means of a liquid ring pump in which phosgene-containing solvent is used as working fluid and then recovering the used working fluid by returning it to the process stage.

Liquid ring pumps are commercially available and have been described, for example, in Siemens catalogue for "ELMO-Gas pumps" (Catalogue No. BK 8.0 P 272), pages ½, ⅓ and ¼.

The use of a liquid ring pump which is operated on an organic solvent as working fluid which is circulated through a heat exchanger to remove the heat generated by operation of the pump is known in principle but has not previously been described for the production of a vacuum for the distillation of solutions which contain phosgene. It may be predicted that part of the phosgene from the distillation apparatus would enter the working fluid of the liquid ring pump, where it would reduce the efficiency of the pump due to its high vapour pressure. The organic solvent used as working fluid must be continuously replaced by purified solvent while the contaminated solvent is treated to recover pure solvent.

Evaporation of the phosgene-containing solvent may also be carried out in a plurality of compression and concentrating stages. The process may advantageously be applied quite generally to any stage in a process for the production of nitrogen or oxygen compounds which must be carried out under a Vacuum while phosgene is present in the waste gases, independent of whether the material introduced into the given distillation stage still contains a large quantity of solvent or only a little or whether the distillation is the final distillation stage of a nitrogen or oxygen compound in which any phosgene still present in a bound from may be split off.

In one particular embodiment of the process according to the invention, the phosgene-containing distillate is split up into a solvent which is free from phosgene or only contains a low concentration of phosgene and a solvent with a high concentration of phosgene, and the solvent with the high phosgene concentration is used as the working fluid. This method reduces the effort required for separation into solvent with a high phosgene concentration and purified solvent.

One variation of the process is characterised in that instead of using the solvent with high phosgene concentration as the working fluid, the solvent with little or no phosgene is used as the working fluid.

This variation has the advantage that most of the phosgene need not be carried through the pump and it is therefore possible to use a small pump with reduced heat generation.

In another special method of carrying out the process according to the invention, the heat produced by the opperation of the liquid ring pump is transferred to a partial stream of the phosgene-containing solvent leaving the liquid ring pump, and this partial stream is returned to the pump together with solvent in which phosgene has concentrated.

alternatively, the partial stream which has been branched off is returned to the liquid ring pump together with solvent which contains little or no phosgene.

The last two methods of carrying out the process described above are based on the use of an internal cooling circuit. The solvent returned to the phosgene absorption or recovery stage is thereby precooled and can therefore absorb more efficiently without requiring additional cooling.

The process according to the invention is represented schematically in a drawing by way of example and described in more detail below. In the drawing, FIG. 1 represents a flow diagram of the process, FIG. 2 is a longitudinal section through the liquid ring pump and FIG. 3 is a cross-section through the liquid ring pump of FIG. 2, and FIGS. 4 to 6 represent variations of the flow diagram of the process.

According to the flow diagram represented in FIG. 1, a nitrogen or oxygen compound 1 is dissolved in a solvent 2 and reacted with a phosgene solution 3 in a phosgenation apparatus 4 from which hydrogen chloride, phosgene and solvent 5 escape into an absorber 6. Used phosgene is replaced by gaseous or liquid phosgene 7. The solution 8 leaving the phosgenation apparatus 4, which contains phosgene, solvent and higher boiling compounds, enters an evaporator 9 in which it separates into a concentrate 10 and a distillate 11. Solvent 2 with a low phosgene content and a vapour mixture 13 of phosgene and solvent are obtained by fractional condensation in a condenser 12. This mixture 13 is cooled in a heat exchanger 14 and then introduced, partly as liquid 15 and partly as gas 16, into a liquid ring pump 17 which produces the vacuum for the evaporator 9. The mixture 18 of liquid and gas leaving the liquid ring pump 17 is fed into a separator 19. The liquid 20 leaving this separator 19 serves as washing liquid for the phosgene gases 5 and 7 introduced into the absorber 6. The waste gases 21 from the liquid ring pump 17 which do not contain absorbed phosgene are also passed through the absorber 6 for further purification. The residual gases 22 leaving the absorber 6 contain only insignificant quantities of phosgene and solvent in addition to hydrogen chloride.

Figures 2, 3:
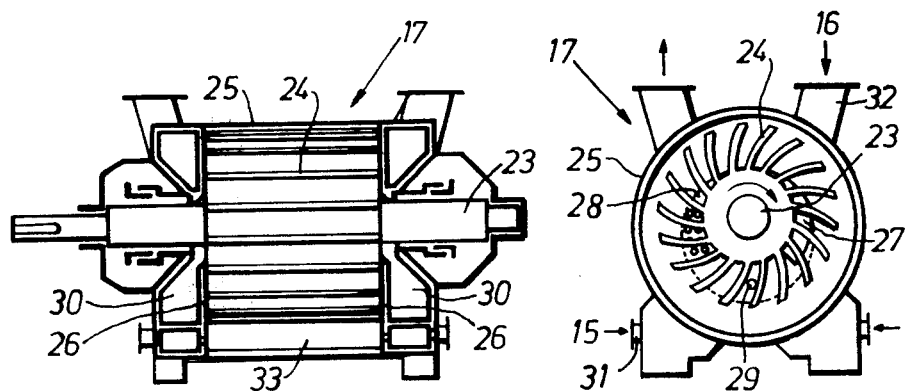

The liquid ring pump 17 represented in FIGS. 2 and 3 comprises a paddle wheel 24 which is keyed to a shaft 23 and eccentrically situated in a housing 25. Control slides 26 with suction slots 27 and pressure slots 28 and apertures 29 for the introduction of flow medium are arranged on both sides of the paddle wheel 24. The space in which the liquid collects is indicated at 30. The liquid 15 is introduced into the pump 17 through the connections 31. Gas 16 enters the pump 17 through the connection 32. The working space 33 is partly filled with liquid. The liquid is flung outwards by rotation of the paddle wheel 24 to form a ring of liquid which rotates with the wheel and is held in by the housing 25 and by the control slides 26 on each side. The ring of liquid demarcates cells between the paddles of the paddle wheel, and these cells increase and decrease in size as the wheel rotates. Due to the eccentric positioning of the shaft 23, the sections of liquid between the blades act as pistons which alternately absorb and expel the gas which has to be conveyed through the pump.

The description given above contains only those stages of the process for the continuous reaction of a nitrogen or oxygen compound in an inert solvent with excess phosgene accompanied by liberation of hydrogen chloride and evaporation of the resulting solution of phosgene, solvent and reaction products in a vacuum which are necessary for an understanding of the inventive idea.

The specific nature of the organic compound introduced into the apparatus, whether it is a primary or secondary aromatic or aliphatic amine, an aliphatic alcohol, a phenol or some other compound which contains a mobile hydrogen atom which is reactive with phosgene, is immaterial to the process.

The following are examples of nitrogen compounds obtained from excess phosgene and primary amines: Phenyl isocyanate, p-chlorophenylisocyanate, 3,4-dichlorophenylisocyanate, 1-naphthylisocyanate, laurylisocyanate, stearylisocyanate, tolylene-2,4-diisocyanate, diphenylmethane-4,4'-diisocyanate, naphthylene-1,5-diisocyanate, hexamethylene diisocyanate and isophorone diisocyanate.

The following are compounds which are obtained from starting materials with secondary nitrogen atoms: Dibutylcarbamic acid chloride, diphenyl-carbamic acid chloride, 2-methylchlorocarbamyl-4-isocyanatotoluene, 1-ethylchlorocarbamyl-naphthylene.

Butyl chloroformate, benzyl chloroformate, phenyl chloroformate, diethylcarbonate and diphenylcarbonate are examples of products of an oxygen compound and phosgene.

Suitable solvents are any known solvents for phosgenating reactions, especially hydrocarbons and chlorinated hydrocarbons such as hexane, carbon tetrachloride, benzene, toluene, chlorobenzene, o-dichlorobenzene and p-dichlorobenzene. If the phosgenation is carried out at a pressure above atmospheric pressure in the phosgenation apparatus 4, then readily volatile inert compounds such as ethane, propane chloromethane or trifluorochloromethane may be used. The practical details of the construction of the parts of the plant described are also unimportant for the process, with the exception of the liquid ring pump 17. Thus, for example, the phosgenation of the nitrogen or oxygen compound 1 introduced as the starting material may be carried out in tanks, towers, reaction loops with pump circulated solutions or any other suitable apparatus. The absorber 6 may be a column filled with packing material or partition plates which may be equipped with heat exchangers either inside or outside the column to remove the heat of absorption. The evaporator 9 may be combined with a column by means of which the solvent may be separated from more highly boiling nitrogen compounds or oxygen compounds. The solvent 2 discharged from the condenser 12 may be passed through a distillation column to remove any residues of dissolved phosgene, phogene-containing solvent being obtained at the head of the column phosgene-containing substantially phosgene free solvent at the base. It is immaterial whether cooling of the condenser 12 is carried out with water, air or another medium. The evaporator 9 and heat exchanger 14 may be operated with water but also with cooling brine or a cooling medium which evaporates in the apparatus, such as ammonia, dichloromonofluoromethane or difluoromonochloromethane.

The liquid ring pump 17 must fulfil two conditions. It must not consist of any parts which are not resistant to the solvent and it must be secured against the escape of phosgene. Commercial pumps, e.g. the ELMO pumps manufactured by Siemens and the pumps manufactured by Nash fulfil these conditions.

In these models, the drive shaft 23 is sealed by means of slide ring packings. The liquid used as sealing fluid and cooling fluid for these packings may be either a partial stream of liquid from the heat exchanger 14 or solvent 2 containing little or no phosgene from condenser 12.

A partial stream of liquid from the heat exchanger 14 may also by-pass the liquid ring pump 17 and be combined directly with the stream 20 of liquid from the pump 17 if the dimensions of the pump require this.

Alternatively, a partial stream of liquid from the pump 17 may be circulated through a heat exchanger so that the heat produced by driving and absorption of the phosgene in the pump 16 is removed in a closed system. If necessary, pressure increasing pumps may, of course, be installed in the various product streams to overcome the differences in liquid levels.

The vacuum produced by the pump 17 can be improved by introducing a gas jet vacuum pump between the heat exchanger 14 and the pump 17. The jet pump absorbs a partial stream of residual gases 21 as working fluid and by means of a jet nozzle it produces a vacuum which is below the suction pressure of the pump 17. Further improvement of the vacuum can be achieved by introducing a rotary piston blower between the heat exchanger 14 and the gas jet mechanism mentioned above.

The term "vacuum" is to be understood to be relative to the pressures in the parts 4 (phosgenation) and 6 (phosgene absorption) of the plant. If, for example, the stream 20 of residual gas from the absorber 6 is restricted to such an extent that an excess pressure of 1 atmosphere is produced at the point of restriction, and if the evaporator 9 is required to be operated at normal pressure, that is to say at an external pressure of 1 atmosphere, then the pump 17, which may be assisted by the gas jet vacuum pump and rotary piston blowers, is required to overcome a pressure interval from pump 17 to absorber 6 of more than 1 atmosphere, 1 atmosphere excess pressure minus 1 atmosphere external pressure in addition to pressure losses in the apparatus 4, 6, 12 and 14.

There is in principle no limit to the pressure range within which the arrangement according to the invention may be used. For practical purposes, however, the evaporator 9 should be operated at a pressure within the range of 5 and 2000 mm Hg, preferably between 50 and 500 mm Hg, for separating a solvent which contains phosgene from compounds which contain nitrogen.

The temperature range within which the pump 17 is operated depends on the vapour pressure of the solvent used and the pressure at which the evaporator 9 is required to operate. For economical reasons, it is desirable to use cooling water or air for cooling in the heat exchanger 14, but if the temperatures which can be obtained in this way are not sufficiently low, cooling with refrigerating machines will be necessary. Again, no fixed temperature limits can be set on principle. A temperature suitable for practical requirements for the liquid 15 leaving the heat exchanger 14 to enter the pump 17 lies between −40°C and 50°C, temperatures of between −20° and 20°C being in most cases satisfactory.

The rate of throughput of material and the size of the apparatus described for evaporating solutions which contain phosgene depend on the dimensions of the whole plant used for producing nitrogen containing compounds. The usual commercial liquid ring pumps have an intake capacity of between 10 and $10^5$ m$^3$ of gas per hour.

The new process has the following advantages compared with conventional systems for producing a vacuum for the evaporation of solutions which contain phosgene: No production of effluent water and contaminated air, no solvent losses, high operational safety, high degree of adaptability to suitable operating conditions as regards pressure, temperature and rate of material throughput, and low energy consumption because any degree of coldness not used for production of the vacuum can be transferred to the absorber 6 with the liquid 20 and used there for the absorption of phosgene.

Figure 4:
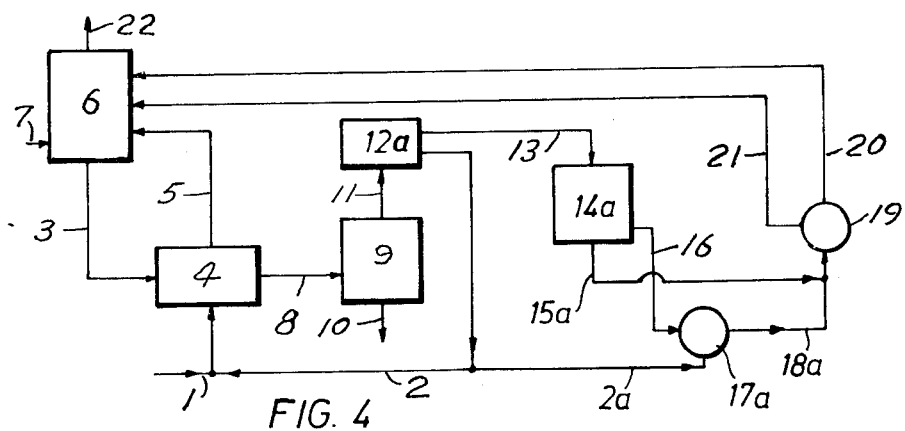

In the variation of the process represented in FIG. 4, the liquid 15a leaving the heat exchanger 14a is not fed into the liquid ring pump 17a as in FIG. 1 but by-passes the pump 17a and is fed into the mixture 18a leaving the pump. To make up for this, a partial stream 2a is branched off the stream of solvent which is low in phosgene content or free from phosgene leaving condenser 12a, and this partial stream 2a is introduced as working fluid into the liquid ring pump 17a. The operation of the process is otherwise the same as represented in FIG. 1.

Figure 5:
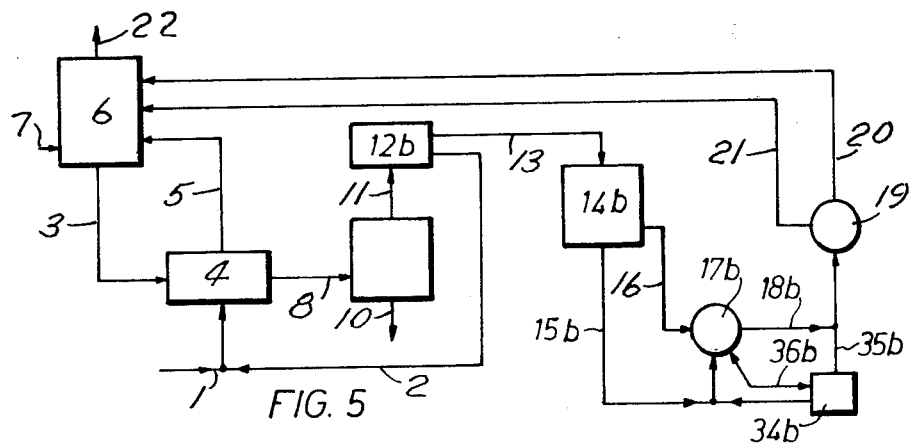

In the variation of the process represented in FIG. 5, the liquid ring pump 17b is connected to a cooling 34b. A partial stream 35b of the mixture leaving the pump 17b is branched off and introduced into the cooler 34b. After being cooled, this partial stream 35b is returned to the pump 17b together with the liquid from the heat exchanger 14b. The reference numeral 36b indicates a circulation for cooling fluid. The process otherwise operates in the same way as represented in FIG. 1.

Figure 6:
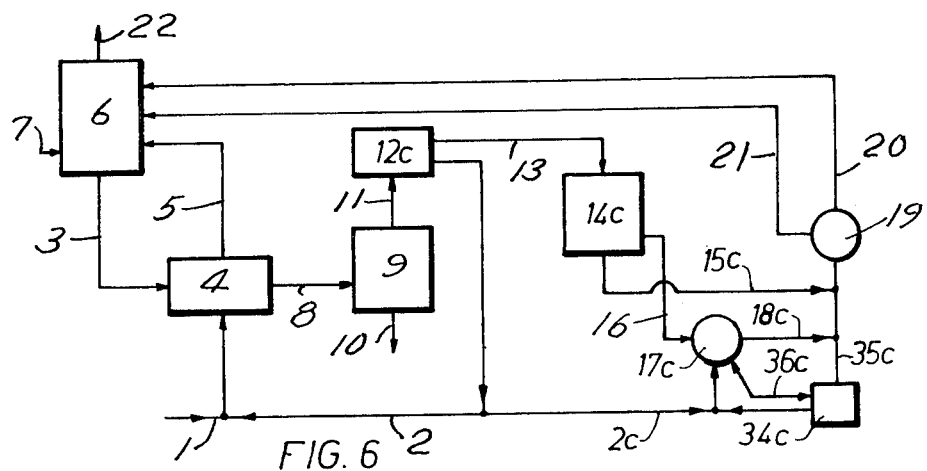

The variation of the process represented in FIG. 6 is based on the scheme represented in FIG. 5. Here again, a partial stream 35b is branched off the mixture 18c leaving the pump 17c and is passed through the cooler 34b. In this case, however, phosgene-containing liquid 15c leaving the heat exchanger 14c by-passes the pump 17c and is directly introduced into the mixture 18c. To make up for this, a partial stream 2c is branched off the stream of solvent which contains little or no phosgene leaving the condenser 12c and is introduced into the pump 17c together with the cooled partial stream 35b. The reference numeral 36b indicates a circulation for cooling fluid.

EXAMPLE 1

(Parts correspond to the rate of throughput in kg/hour).

A solution of 14 parts of phosgene, 3000 parts of chlorobenzene and 400 parts of diphenylmethane diisocyanate mixed with higher nuclear homologues is concentrated in an evaporator 9 at a pressure of 160 mm Hg to produce a concentrate 10 consisting of 15 parts of chlorobenzene and 400 parts of isocyanate mixture. The vapours 11 are precipitated in an air cooled condenser 12. A partial stream of 1800 parts of chlorobenzene 2 is returned to the reaction cycle and serves to dissolve the amine mixture 1. The distillate 12 which contains phosgene is cooled to about −20° to −5°C with brine in the heat exchanger 14 and part of the distillate is introduced as working fluid 15 into a Siemens ELMO 2 BA 212 liquid ring pump 17 which produces a vacuum for the distillation system. Combined with the heat exchanger 14, the phosgene-containing chlorobenzene is introduced into an absorber 6 in which it serves to absorb unused phosgene 4 from the phosgenation apparatus 4 and fresh phosgene 7. The waste gases 21 from the liquid ring pump 17 are also passed through the absorber 6. The residual gas 22 obtained as head product of this absorber consists of the purified hydrogen chloride gas resulting from the reaction of the amine with phosgene. The sump product 3, a solution of phosgene in chlorobenzene, is introduced into the phosgenation apparatus 4.

What we claim is:

1. A process for the evaporation in a vacuum of a solution containing phosgene, a solvent selected from the group consisting of liquid hydrocarbons and chlorohydrocarbons with a boiling point under atmospheric pressure of about 100°C and a compound selected from the group consisting of organic isocyanates, chlorocarbonic acid esters and carbonates with a boiling point under atmospheric pressure of above 160°C which is higher boiling than said solvent in which process the vacuum is produced by a vacuum liquid ring pump which uses said phosgene-containing solvent as the sealant fluid at a temperature of −40° to 50°C, and in which the used sealant fluid is returned to the process which generates said solution.

2. A process as claimed in claim 1, in which the phosgene-containing distillate is separated by condensation into a solvent which contains less than about 0.1 wt. % phosgene and a solvent which has a phosgene concentration of more than about 0.5 wt. %, the solvent with the higher phosgene concentration being used as the working fluid.

3. A process as claimed in claim 1, in which the phosgene-containing distillate is separated by condensation into a solvent which contains less than about 0.1 wt. % phosgene and a solvent which has a phosgene concentration of more than about 0.5 wt. %, the solvent with the lower phosgene concentration being used as the working fluid.

4. A process as claimed in claim 2, in which the heat produced by the operation of the liquid ring pump is transferred to a partial stream of the phosgene-containing solvent leaving the liquid ring pump and this partial stream is returned to the liquid ring pump together with the solvent which has a higher phosgene concentration 5. A process as claimed in claim 3, in which the heat produced by the operation of the liquid ring pump is transferred to a partial stream of the phosgene-containing solvent leaving the liquid ring pump and this partial stream is returned to the liquid ring pump together with the solvent which contains less than about 0.1 wt. % phosgene.

* * * * *